United States Patent [19]

Silvestrini

[11] Patent Number: 4,749,684

[45] Date of Patent: Jun. 7, 1988

[54] METHOD FOR INCREASING HAIR GROWTH

[76] Inventor: Bruno Silvestrini, Via Michelangelo Schipa 15, Rome, Italy, 00179

[21] Appl. No.: 779,515

[22] Filed: Sep. 24, 1985

Related U.S. Application Data

[63] Continuation-in-part of Ser. No. 540,812, Oct. 11, 1983, abandoned, which is a continuation of Ser. No. 262,840, May 12, 1981, abandoned.

[30] Foreign Application Priority Data

May 30, 1985 [IT] Italy ............................. 20977 A/85

[51] Int. Cl.⁴ ............................................. A61K 37/00
[52] U.S. Cl. ....................................................... 514/2
[58] Field of Search ............................................ 514/2

[56] References Cited

PUBLICATIONS

Scala et al.–Nutrit. Report Internat., vol. 13 (1972), pp. 579–592.

*Primary Examiner*—Sam Rosen
*Attorney, Agent, or Firm*—Ladas & Parry

[57] ABSTRACT

The invention herein is directed to a method of increasing the linear growth rate of hair by administering gelatin over a long period of time.

3 Claims, No Drawings

METHOD FOR INCREASING HAIR GROWTH

This is a continuation-in-part of co-pending application Ser. No. 540,812 filed Oct. 11, 1983 now abandoned which is a continuation of co-pending application Ser. No. 262,840 filed May 12, 1981, now abandoned.

The present invention relates to a method for treating disorders of the scalp, such as thinning or fall of hair; it is based on the addition of gelatin (jelly) to foodstuffs at a dosage of 8-16 grams per daily portion.

It is a known fact that food deficiencies can cause a weakening, a thinning and a fall of hair; these deficiencies alone or concomitantly with other factors, such as stress, aging, topical or systemic diseases, pharmaceutical treatments, are the causative factors. In order to correct these conditions it has been suggested that the administration of gelatin could be considered the proper remedy, since the latter contains in almost optimal proportion the necessary aminoacids for the growth of hair. The available information on this topic can be summarized as follows:

1. Scala et al. (Scala, J., Hollies, N. R. S. and Sucher, K. P., Effect of daily gelatin ingestion on human scalp hair, Nutr. Report Inter., 1976, 13: 579-592) have studied the effects produced by the administration of 14 grams daily of gelatin in man. After 62 days of treatment these authors did not notice any effect on the growth of hair; they could only note an improvement in the structural properties of hair.

2. In the patent titled "Metodo per il trattamento di disturbi del sistema pilifero in mammiferi" (Method for the treatment of disorders of the piliferous system in mammals) and deposited on 33.2.1981 (N. 19917 A/81), this author of the patent reported that the administration of gelatin in the dosage of 100-500 mg/kg (milligrams per kg of body weight) increases the growth of hair in the skin of the rat, the dog, the rabbit and the cat.

On the basis of these results the author has vindicated the claim that gelatin can be used in man since the experimental results obtained in animals suggest that similar conditions apply in humans.

3. The fact that Scala et al. (1976) could not observe an effect from gelatin administration on the growth of hair, is attributed to the duration of treatment. In fact, the increase of hair growth in the rat is noted only after continuous administration of gelatin for two weeks, whereas it takes 4-8 weeks for the cat and the dog. After due consideration to the different life span between these animal species and man, it is appropriate to arrive at a calculation giving a minimum period of three months' administration of gelatin for man in order to obtain the results seen in animals.

4. It must be mentioned that a favorable effect on the growth of hair has been reported also by Morganti et al. (Morganti, P., Randazzo, S. and Bruno, C., Effect of gelatin-cystine on hair growth, J. Soc. Cosm. Chem., 1982, 33: 95-96) in men treated with a low dosage of gelatin combined with a relatively high dosage of cystine. This study, however, does not appear to be relevant in respect to this patent since, based on our experiment, the low dosages of gelatin employed by Morganti et al. are not sufficient to produce an effect on the growth of hair: consequently, the effect reported by those workers must be attributed to the administration of cystine.

In order to find a practical application of the invention claimed in the patent above-mentioned in paragraph 2, we have undertaken experimental-controlled studies in humans, but have become aware of the fact that many persons have difficulty to ingest the necessary quantity of gelatin whenever this is administered in a form of capsules or other pharmaceutical formulations. This difficulty can be so serious as to limit substantially the possibility to translate the benefits of this invention into a practical implementation. Therefore, a method had to be found based on enriched foodstuffs to which the appropriate quantity of gelatin, necessary for the promotion of hair growth, had been added.

EXPERIMENTAL DESIGN

A first study has been completed on 40 healthy volunteer subjects (20 males and 20 females) of age comprised between 18-28 years. These volunteers were subdivided into two homogeneous groups by age and body weight. The first group received 8 grams of gelatin daily; the second, an equal amount of starch. Both the gelatin and the starch were contained in standard 1 gram capsules. The linear growth of the hair was measured according to the method of Scala, (1976) with certain modifications. Prior to the beginning of the experiment, each and every volunteer was subjected to a limited shaving of the head in the median occipital region, this area having been chosen for reasons of aesthetics, in order to better hide the shaved area. Following beginning of treatment, the same area was again shaved every month, ensuring that from each subject an average of 10 hairs were collected. The effects of gelatin were evaluated comparing the growth of hair in the gelatin-treated group versus the group that had received the starch. The study was doubleblind inasmuch as the investigators measuring the length of hair in each subject were not aware of the type of treatment received by the subject in question. At the end of treatment, each volunteer was asked to express a judgment on the effect of the treatment from the aesthetic point of view of their hair. The statistical analysis was conducted according to the t Student test.

In this first study, 28 subjects out of 40 dropped out from the experiment because the ingestion of capsules was found to be bothering and/or some side-effects appeared such as heartburn, gastric intolerance and, in some subjects, vomit and dizziness. These side-effects were equally distributed between the two groups, i.e. the ones treated with starch and the ones treated with gelatin. A second study was undertaken identical to the first one from every point of view with the exception of the way in which the experimental substances were administered and the criteria for choosing the experimental population. In this second study, both gelatin and starch were administered not any longer in the form of capsules but by mixing them in an ordinary jar of commercial yogurt. This was to be eaten in the morning, for breakfast, and the subjects chosen were men and women who were in the habit of having yogurt for breakfast.

This study was brought to completion and the results can be seen in the following table:

TABLE I

EFFECTS OF GELATIN ON THE GROWTH OF HAIR

| | Months and hair length (median in mm) | | |
| --- | --- | --- | --- |
| | 1 | 2 | 3 |
| Control | 10.9 | 11.1 | 10.9 |

TABLE I-continued
EFFECTS OF GELATIN ON THE GROWTH OF HAIR

| | Months and hair length (median in mm) | | |
|---|---|---|---|
| | 1 | 2 | 3 |
| Gelatin | 11.4(*) | 11.7(*) | 12.2(**) |

*Statistically insignificant
**Statistically significant (0.05)

In the group treated with gelatin, the growth of hair is significantly higher than in the control group after three months of treatment; whereas the difference between the two groups is not statistically significant either at one or two months. Upon completion of the trial, 16 of the 20 subjects who had received gelatin reported that the structure and the aspect of their hair had improved; whereas only 4 out of 20 of the starch-treated group reported a similar impression.

Tolerance was good in all cases.

The results of this study show that the daily ingestion of foodstuffs containing 100 mg/kg (body weight) of gelatin, is a simple and effective method for the administration of those animoacids which are necessary for enhanced growth of hair in man. In the above study, the gelatin had been mixed into the yogurt; however, it is clear that the same method of administration can be applied to other foodstuffs. The only requirement being that these foodstuffs be available in containers which will ensure the administration of a constant dosage of gelatin. The treatment must be of not less than 3 months because alternatively, as previously shown by Scala et al. (1976), the effect on the growth of hair does not appear.

I claim:

1. A method for increasing the linear growth rate of hair comprising administering to a patient in need of such treatment not less than 100 mg/kg body weight of gelatin for at least 3 months in humans and at least 8 weeks for a cat or dog.

2. A method as in claim 1 wherein said gelatin is administered in foodstuff.

3. A method as in claim 2 wherein said foodstuff comprises yogurt.

* * * * *